United States Patent
Cherfils et al.

(10) Patent No.: US 8,772,243 B2
(45) Date of Patent: Jul. 8, 2014

(54) METHODS FOR PREDICTING THE RESPONSE TO ANTI-CANCER TREATMENT WITH AN AGONIST OF TLR7 OR AN AGONIST OF TLR8

(75) Inventors: Julien Cherfils, Paris (FR); Herve Fridman, Paris (FR); Isabelle Cremer, Paris (FR)

(73) Assignee: Inserm (Institut National de la Sante et de la Recherche Medicale), Paris (FR)

( * ) Notice: Subject to any disclaimer, the term of this patent is extended or adjusted under 35 U.S.C. 154(b) by 264 days.

(21) Appl. No.: 13/058,113

(22) PCT Filed: Aug. 14, 2009

(86) PCT No.: PCT/EP2009/060555
§ 371 (c)(1),
(2), (4) Date: Apr. 27, 2011

(87) PCT Pub. No.: WO2010/020590
PCT Pub. Date: Feb. 25, 2010

(65) Prior Publication Data
US 2011/0195923 A1      Aug. 11, 2011

(30) Foreign Application Priority Data
Aug. 20, 2008   (EP) .................................. 08305490

(51) Int. Cl.
*A61K 38/00* (2006.01)
*A61P 35/00* (2006.01)
*G01N 33/53* (2006.01)

(52) U.S. Cl.
USPC .......................................... 514/19.3; 435/7.1

(58) Field of Classification Search
None
See application file for complete search history.

(56) References Cited

U.S. PATENT DOCUMENTS

| 2006/0147456 A1 | 7/2006 | Lebecque et al. |
| 2009/0202626 A1 * | 8/2009 | Carson et al. ................. 424/450 |

FOREIGN PATENT DOCUMENTS

| WO | 2007/042554 | 4/2007 |
| WO | 2007/100650 | 9/2007 |
| WO | 2008/009693 | 1/2008 |

OTHER PUBLICATIONS

Peris et al., Dermatol Surg., 2005, 31:318-323.*
Smits et al., The Oncologist , 2008, 13: 859-875.*
Basith et al., Arch Pharm Res., 2012, 35(8):1297-1316.*
Dunne et al., Curr Opin Pharmocol., 2011, 11:404-411.*
Jego et al., Leukemia, 2006, 20:1130-1137.*
Conroy et al., Oncogene, 27(2):168-180 (2008).
International Search Report and Written Opinion in PCT/EP09/60555, dated Dec. 16, 2009.
Salaun et al., Eur. J. Immunol., 37(12):3311-3318 (2007).
Schon et al., Oncogene, 27(2):190-199 (2008).
Wang et al., Oncogene, 27(2):181-189 (2008).

* cited by examiner

*Primary Examiner* — Hong Sang
(74) *Attorney, Agent, or Firm* — McAndrews, Held & Malloy Ltd.

(57) ABSTRACT

The present invention relates to methods for predicting the response to treatment with an agonist of TLR7, or an agonist of TLR8 or an anti-cancer agent for treating cancer, in particular non-small cell lung cancer comprising the step of detecting the expression of TLR7 or TLR8 in cancer cells of said patient.

4 Claims, 7 Drawing Sheets

METHODS FOR PREDICTING THE RESPONSE TO ANTI-CANCER TREATMENT WITH AN AGONIST OF TLR7 OR AN AGONIST OF TLR8

The present application is filed pursuant to 35 U.S.C. 371 as a U.S. National Phase application of International Patent Application No. PCT/EP09/60555, which was filed Aug. 14, 2009, claiming the benefit of priority to European Patent Application No. 08305490.8, which was filed on Aug. 20, 2008. The entire text of the aforementioned applications is incorporated herein by reference in its entirety.

FIELD OF THE INVENTION

The present invention relates to methods for predicting the response to treatment and for treating cancer, in particular non-small cell lung cancer.

BACKGROUND OF THE INVENTION

Cancer is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). Cancer represents one of the leading causes of death in the world.

Cancers can be classified according to the organ, tissue and cell-type from which the cancerous cells originate: lung, colon, liver, skin etc.

Lung cancer is the leading cause of cancer-related deaths throughout the world. Among those, non-small cell lung cancer (NSCLC) represents 80% of the cases. The size of the primary tumor, the invasion of loco-regional nodes and, the presence of distant metastases, determine the survival rate. These parameters are used to define the stage of the disease and to decide the optimal patient management.

In spite of the progress in medical and surgical treatments, long term survival remains poor, with overall values ranging from 20 to 30% at 5 years after surgery. Patients generally relapse within 3 years, with the development of metastases.

Currently available therapies for lung cancer are neo-adjuvant chemotherapy followed by surgery (the chemotherapy being decided if the patient is not operable or presents an invasion of the mediastinal ganglions), or surgery alone. In both cases, the surgical intervention can be followed by chemotherapy in order to eradicate any residual tumor cells.

Novel cancer therapies are being developed which are based on the amplification of the immune response.

Toll-Like Receptors (TLR) are cell-surface or endogenous receptors by which cells recognize Pathogen Associated Molecular Patterns (PAMP) (Killen SD 2006). These receptors are involved in the recognition of molecular patterns, such as single-stranded and double-stranded RNA, double-stranded DNA, LPS, lipoteichoic acid, etc . . . and are mainly expressed by cells of the immune system.

Immunotherapeutic treatments based on the use of TLR9 ligands are currently being tested for the treatment of solid cancers, such as NSCLC (Kanzler H. et al. 2007 Nature Medicine, 13:532; Krieg A. M. 2007, JCI, 117:1184).

U.S. patent application Ser. No. 11/184,191 to Lebecque et al. describes methods for treating Toll-like receptor expressing cancers and tumor cells by selecting a TLR expressing tumor cell and contacting the cell with a therapeutically effective amount of a TLR ligand. In particular, Ser. No. 11/184,191 describes methods for treating TLR3 expressing cancers and tumors cells using TLR3 agonists. The TLR3 agonist induces apoptosis of the tumor cells expressing TLR3.

Another treatment currently under investigation is the use of TLR7 or 8 agonists as adjuvants to prime the antitumoral immune responses. The lead compound of the imidazoquinoline family, imiquimod, is marketed as a topical formulation for use against primary skin tumors and cutaneous metastasis (Schön & Schön, Oncogene, 2008). In skin cancer, there is relative efficacy which is mainly due to increased immune functions, particularly enhancement of Natural Killer cell antitumor activity, dendritic cell maturation and T cell immunity to tumor antigens (Schön 2008, Kanzler 2007, Stary 2007). In contrast, treatment with a TLR7 agonist does not influence the clinical outcome in metastatic melanoma (Dummer et al., 2008). Research efforts are being made in order to develop other TLR7 agonists for use as immunotherapeutic agents (Wu et al., 2007, PNAS). However, the efficacy of TLR agonists as adjuvants for cancer therapy remains to be established.

There is still an unmet need for predicting the response to treatment of cancer, and for new therapeutic methods for treating cancer, in particular NSCLC.

SUMMARY OF THE INVENTION

The invention provides a method for predicting the response to a combined treatment with an anti-cancer agent and an agonist of TLR7 or TLR8 in a patient suffering from cancer, comprising the step of detecting the expression of TLR7 or TRL8 respectively in cancer cells of said patient.

Also provided is a method for predicting the response to treatment with an anti-cancer agent in a patient suffering from cancer, comprising the step of detecting the expression of TLR7 or TLR8 in cancer cells of said patient.

The invention also relates to a compound for treating cancer in a patient wherein said compound is an agonist of TLR7 or TRL8 and wherein said patient does not express TLR7 or TRL8 respectively in cancer cells.

The present invention also relates to a method for treating a cancer patient comprising administering a therapeutically effective amount of an agonist of TLR7 or TLR8, wherein said patient does not express TLR7 or TLR8 respectively in cancer cells.

DETAILED DESCRIPTION OF THE INVENTION

Definitions

The expressions "agonist of TLR7" and "agonist of TLR8" refer to compounds which bind to and activate TLR7 or TLR8 respectively. The terms "activation" and "stimulation" are used indifferently.

Those compounds can be natural or synthetic. Many of the compounds that activate TLR7 also activate TLR8. It falls within the ability of the skilled person to determine whether, at a given dose, a compound is specific for one or other of these receptors.

Several agonists of TLR7 or TLR8 are known in the art, many of which are envisaged for use in combined therapy with an anti-cancer agent for the treatment of a patient suffering from cancer.

Methods for identifying agonists of TRL7 or agonists of TLR8 are described for example in document WO2004/075865 (3M Innovative Properties Company).

Natural agonists of TLR7 and TLR8 have recently been identified as guanosine- and uridine-rich ssRNA (Diebold, Science 2004, Heil Science, 2004).

In addition, synthetic agonists of TLR7 include, but are not limited to: imidazoquinoline-like molecules, imiquimod, resiquimod, gardiquimod, S-27609; and guanosine analogues such as loxoribine (7-allyl-7,8-dihydro-8-oxo-guanosine), 7-Thia-8-oxoguanosine and 7-deazaguanosine, UC-1V150, ANA975 (Anadys Pharmaceuticals), SM-360320 (Sumimoto), 3M-01 and 3M-03 (3M Pharmaceuticals) (see for example Gorden et al., J Immunology, 2005; Schön, Oncogene, 2008; Wu et al., PNAS 2007).

Synthetic agonists of TLR8 include 3M-02 (developed by 3M Pharmaceuticals and commercialised for example by Invivogen as CL075), 3M-03, Poly-G containing 10 guanosine nucleosides connected by phosphothioate linkages (Poly-G10).

Preferably the agonist of TLR7 is selected from the group consisting of loxoribine and Poly U. Even more preferably, the agonist of TLR7 is loxoribine.

Preferably the agonist of TLR8 is selected from the group consisting of Gardiquimod and Poly U.

As used herein, the terms "antagonist of TLR7" and "antagonist of TLR8" refer to compounds which inhibit signaling through TLR7 or TLR8 respectively. They include compounds which inhibit TLR7 or TLR8 by binding to said receptors and compounds which inhibit TLR7 or TL8 signaling by other mechanisms.

Typically, antagonists of TLR7 are synthetic compounds such the TLR7/9 antagonist IRS954 developed by Dynavax (see for example Tomai et al., Drug Discovery Today, 2006) or 2'-O-methyl modified RNAs as described in Robbins et al., Molecular Therapy, 2007.

Methods for screening for TLR7 and TRL8 agonists and antagonists are described in documents US 20060269936, U.S. Pat. No. 7,375,180 and WO2005007672.

In a preferred embodiment, the antagonist of TLR7 or TLR8 is selected from the group consisting of 2'-O-methyl-modified RNAs and IRS954.

Antagonists of TLR7 or TRL8 according to the invention can also be small inhibiting RNAs (siRNA) specifically designed against TLR7 or TLR8 respectively. siRNAs can inhibit signaling through a given receptor by lowering the expression level of said receptor.

As used herein, the term "cancer" refers to the pathological condition in mammals that is typically characterized by unregulated cell growth. Examples of cancer include, but are not limited to lung cancer, breast cancer, colorectal cancer, renal carcinoma, prostate cancer, melanoma, and lymphoma.

In a preferred embodiment, said cancer is lung cancer. Even more preferably, said cancer is a non-small cell lung cancer (NSCLC).

In a preferred embodiment, said cancer is diffuse large B-cell lymphoma.

The expression "cancer cells" refers to the population of cells which display uncontrolled growth. It falls within the ability of the skilled artisan to identify the cancer cells which are characteristic of each type of cancer. Many morphological markers and biomarkers are available that allow the identification of cancer cells. For example, in the case of NSCLC, the cancer cells express Epithelial Membrane Antigen (EMA), BrEp4 and AE1-AE3.

As used herein, the term "patient" denotes a mammal, such as a rodent, a feline, a canine, and a primate. Preferably, a patient according to the invention is a human.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of the disorder or condition to which such term applies.

By a "therapeutically effective amount" of an agonist of TLR7 or agonist of TLR8 is meant a sufficient amount to treat cancer, preferably non-small cell lung cancer, at a reasonable benefit/risk ratio applicable to any medical treatment. It will be understood, however, that the total daily usage of agonist of TLR7 or agonist of TLR8 will be decided by the attending physician within the scope of sound medical judgment. The specific therapeutically effective dose level for any particular subject in need thereof will depend upon a variety of factors including the stage of non-small cell lung cancer being treated and the activity of the specific agonist of TLR7 or agonist of TLR8 employed, the age, body weight, general health, sex and diet of the subject, the time of administration, route of administration, the duration of the treatment; drugs used in combination or coincidental with the and like factors well known in the medical arts. For example, it is well known within the skill of the art to start doses of the compound at levels lower than those required to achieve the desired therapeutic effect and to gradually increase the dosage until the desired effect is achieved.

As used herein, the expression "anti-cancer agent" or "chemotherapeutic agent" refers to compounds which are used in the treatment of cancer.

Anti-cancer agents include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin.

In one embodiment, the anti-cancer agent is selected for the group consisting of taxol; taxotere; platinum complexes such as cisplatin, carboplatin and oxaliplatin; doxorubicin; taxanes such as docetaxel and paclitaxel; vinca alkaloids such as vinblastine, vincristine and vinorelbine; genistein; erbstatin; and lavendustin.

Method for Predicting Response to Treatment

The invention provides a method for predicting the response to treatment with an agonist of TLR7 in a patient suffering from cancer, comprising the step of detecting the expression of TLR7 in cancer cells of said patient.

The invention also provides a method for predicting the response to treatment with an agonist of TLR8 in a patient suffering from cancer, comprising the step of detecting the expression of TLR8 in cancer cells of said patient.

Without wishing to be bound by theory, the inventors have discovered that, besides the expected beneficial effect of TLR7 and TLR8 agonists on the stimulation of the immune system, said agonists may have a deleterious effect on certain types of cancer. Indeed, when the cancer cells express TLR7 or TLR8, the TLR7 or TLR8 agonist can exert an additional effect by increasing the tumor cell survival and by conferring resistance to apoptosis induced by chemotherapeutic agents. Hence, when the cancer cells express TLR7 (respectively TLR8) treatment of said cancer with an agonist of TLR7 (respectively TLR8) is to be avoided.

The invention also provides a method for predicting the response to a combined treatment with an anti-cancer agent and an agonist of TLR7 in a patient suffering from cancer, comprising the step of detecting the expression of TLR7 in cancer cells of said patient.

The invention also provides a method for predicting the response to a combined treatment with an anti-cancer agent and an agonist of TLR8 in a patient suffering from cancer, comprising the step of detecting the expression of TLR8 in cancer cells of said patient.

The invention also provides a method for predicting the response to treatment with an anti-cancer agent in a patient suffering from cancer, comprising the step of detecting the expression of TLR7 or TLR8 in cancer cells of said patient.

Typically, the presence of TLR7 or TLR8 in cancer cells is indicative of poor response to treatment. Indeed, the inventor has surprisingly demonstrated that treatment with an agonist of TLR7 or an agonist of TLR8 promotes cancer cell survival. Combined treatment with an agonist of TLR7 or TLR8 associated with an anti-cancer agent is poorly effective when TLR7 or TRL8 are present in cancer cells. Indeed, the inventors have surprisingly demonstrated that the agonist of TLR7 or TLR8 renders the cancer cells resistant to chemotherapy, instead of boosting the immune response of the affected tissue as was previously expected. The presence of TRL7 or TRL8 in cancer cells is also associated with poor response to treatment with anti-cancer agent alone.

Without wishing to be bould by theory, the inventors believe that endogenous stimulation of TLR7 and TLR8 likely occurs within the tumor, so that the presence of high percentages of TLR7 and/or TLR8expression in the cancer cells of a patient is indicative of a poor response to treatment with an anti-cancer agent, a higher risk of developing metastases and a lower survival rate of said patient compared to patients who do not express or express low levels of TLR7 and/or TLR8 in said cancer cells.

In one embodiment, the invention relates to a method for predicting metastatic recurrence in a patient suffering from cancer, comprising the step of detecting the expression of TLR7 or TLR8 in cancer cells of said patient.

In one embodiment, the invention relates to a method for prognosis in a patient suffering from cancer, comprising the step of detecting the expression of TLR7 or TLR8 in cancer cells of said patient.

In one embodiment of the invention, detecting the expression of TLR7 or TLR8 in cancer cells is performed by the following method:
a) obtaining a biological sample containing cancer cells from said patient,
b) detecting the expression TLR7 or TLR8 in said cancer cells in said biological sample.

According to the invention, a biological sample is a sample of the tumor tissue or cancer cells obtained from the patient according to methods known in the art. In the case of solid tumors, the biological sample can be a biopsy. Typically, the biological sample according to the invention is a tumor sample obtained after medical surgery. Typically, the biological sample is a purified cancer cell sample obtained from a tissue sample.

For example, in the case of lung cancer, the biological sample can be a human primary lung tumor sample or purified primary lung tumor cells. In the case of blood cancers, the biological sample can be a blood sample or purified blood cells. In the case of skin cancer, the biological sample can be a skin biopsy or purified melanocytes.

Detecting the expression of TLR7 or TLR8 in cancer cells can be performed by a variety of techniques.

More preferably, the detection comprises contacting the cancer cells of the biological sample with selective reagents such as probes, primers, ligands or antibodies, and thereby detecting the presence of nucleic acids or proteins of interest originally in the sample.

In a preferred embodiment, the expression may be detected by detecting the presence of mRNA.

Methods for detecting the presence of mRNA are well known in the art. For example the nucleic acid contained in the samples (e.g., isolated cancer cells prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). In a preferred embodiment, the expression of the TLR7 gene or TLR 8 is detected by RT-PCR, preferably quantitative or semi-quantitative RT-PCR, even more preferably real-time quantitative or semi-quantitative RT-PCR.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise contacting the cancer cells of the biological sample with a binding partner capable of selectively interacting with the TLR7 or TLR8 protein present in the biological sample. The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce anti-TLR7 or anti-TLR8 single chain antibodies. Antibodies useful in practicing the present invention also include anti-TRL7 fragments and anti-TLR8 fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to TLR7 or TLR8. For example, phage display of antibodies may be used. In such a method, single-chain Fv (scFv) or Fab fragments are expressed on the surface of a suitable bacteriophage, e.g., M13. Briefly, spleen cells of a suitable host, e.g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e.g., bacteria, the phage displays the antibody fragment. Phage display of antibodies may also be provided by combinatorial methods known to those skilled in the art. Antibody fragments displayed by a phage may then be used as part of an immunoassay.

Antibodies against TLR7 and TLR8 are available from Alexis (Grünberg, Germany) (rabbit polyclonal anti-TLR7 and monoclonal anti-TLR8 antibody clone 44C143).

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention, such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays generally involve the binding of the binding partner (ie. Antibody or aptamer) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

The expression of the TLR7 or TLR8 protein in cancer cells may be measured by using standard immunodiagnostic techniques, including immunoassays such as competition, direct reaction, or sandwich type assays. In such embodiments, cancers cells are purified from the isolated biological sample Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of antibodies against TLR7 or TLR8. The cancer cells of the biological sample that are suspected of containing TLR7 or TLR8 are then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Other standard method for isolating cancer cells expression TLR7 or TLR8 consists in collecting cancer cells of the biological sample and using differential antibody binding, wherein cancer cells expressing TLR7 and/or TLR8 are bound by antibodies directed to TLR7 or TLR8. Fluorescence activated cell sorting (FACS) may be therefore used to isolate and quantify the cancer cells expressing TLR7 or 8. In another embodiment, magnetic beads may be used to isolate cancer cells expressing TLR7 or 8 (MACS). For instance, magnetic beads labelled with monoclonal cell type specific antibodies may be used for the positive selection of cancer cells expressing TLR 7 or 8.

In a preferred embodiment, detecting the expression of TLR7 or TLR8 in cancer cells of the patient is carried out by immunohistochemistry performed on a biopsy or after medical surgery.

In another embodiment, detecting the expression of TLR7 or TLR8 in the cancer cells of a patient can be performed by subjecting said patient to imaging after administration of a quantity sufficient for imaging of a labelled agent which binds to TLR7 or TLR8. It falls within the ability of the skilled artisan to carry out such an imaging method. Typically, the label may be a fluorophore, a radioactive isotope or a paramagnetic agent.

The term "agents which bind to TLR7 or TLR8" includes agonists of TLR7 or TLR8 and antagonists of TLR7 or TLR8. On the one hand, agonists of TLR7 or TLR8 have been described above. On the other hand, 2'-O-methyl-modified RNAs act as TLR7 antagonists (Robbins et al, Molecular Therapy).

In a particular embodiment, the cancer is selected from the group consisting of breast cancer, colorectal cancer, renal carcinoma, prostate cancer, melanoma, and lymphoma, such as lung cancer, for example non-small cell lung cancer.

In a particular embodiment, the agonist of TLR7 is selected from the group consisting of loxoribine and Poly U, preferably loxoribine.

In a particular embodiment, the agonist of TLR8 is selected from the group consisting of Gardiquimod and Poly U.

In some embodiments, the anti-cancer agent is selected from taxol; taxotere; platinum complexes such as cisplatin, carboplatin and oxaliplatin; doxorubicin; taxanes such as docetaxel and paclitaxel; vinca alkaloids such as vinblastine, vincristine and vinorelbine; genistein; erbstatin; and lavendustin.

Therapeutic Method

The present invention relates to a method for treating a cancer patient comprising administering a therapeutically effective amount of an agonist of TLR7 or TLR8, wherein said patient does not express TLR7 or TLR8 respectively in cancer cells.

In other terms, the invention relates to the use of an agonist of TLR7 or TLR8 for the manufacture of a medicament for treating cancer in a patient wherein said patient does not express TLR7 or TRL8 respectively in cancer cells.

The invention also relates to an agonist of TLR7 for treating cancer in a patient wherein said patient does not express TLR7 in cancer cells.

The invention also relates to an agonist of TLR8 for treating cancer in a patient wherein said patient does not express TLR8 in cancer cells.

In a particular embodiment, the agonist of TLR7 is selected from the group consisting of loxoribine and Poly U, preferably loxoribine.

In a particular embodiment, the agonist of TLR8 is selected from the group consisting of Gardiquimod and Poly U.

In a preferred embodiment, the agonist of TRL7 or TLR8 is used in combination with chemotherapy, i.e. in combination with an anti-cancer agent. In a preferred embodiment, the anti-cancer agent is selected from taxol; taxotere; platinum complexes such as cisplatin, carboplatin and oxaliplatin; doxorubicin; taxanes such as docetaxel and paclitaxel; vinca alkaloids such as vinblastine, vincristine and vinorelbine; genistein; erbstatin; and lavendustin.

The present invention relates to a method for treating a cancer patient comprising administering a therapeutically effective amount of an antagonist of TLR7 or TLR8, wherein said patient expresses TLR7 or TLR8 respectively in cancer cells.

In other terms, the invention relates to the use of an antagonist of TLR7 or TLR8 for the manufacture of a medicament for treating cancer in a patient wherein said patient expresses TLR7 or TRL8 respectively in cancer cells.

The invention also relates to an antagonist of TLR7 for treating cancer in a patient wherein said patient expresses TLR7 in cancer cells.

The invention also relates to an antagonist of TLR8 for treating cancer in a patient wherein said patient expresses TLR8 in cancer cells.

In a preferred embodiment, the antagonist of TLR7 or TLR8 is selected from the group consisting of 2'-O-methyl-modified RNAs and IRS954.

In a preferred embodiment, the antagonist of TRL7 or TLR8 is used in combination with chemotherapy, i.e. in combination with an anti-cancer agent. In a preferred embodiment, the anti-cancer agent is selected from taxol; taxotere; platinum complexes such as cisplatin, carboplatin and oxaliplatin; doxorubicin; taxanes such as docetaxel and paclitaxel; vinca alkaloids such as vinblastine, vincristine and vinorelbine; genistein; erbstatin; and lavendustin.

Methods for determining that whether the patient expresses TLR7 or TLR8 in cancer cells or not can be performed as described above.

Typically medicaments according to the invention comprise an agonist of TLR7 or TLR8 or an antagonist of TLR7 or TLR8 together with a pharmaceutically-acceptable carrier. A person skilled in the art will be aware of suitable carriers. Suitable formulations for administration by any desired route may be prepared by standard methods, for example by reference to well-known text such as Remington; The Science and Practice of Pharmacy.

A method of treatment according to the invention may be used in combination with any other therapeutic strategy for treating cancer, in particular non-small cell lung cancer, e.g. surgery, external radiotherapy, chemotherapy or hormone therapy or cytokine therapy.

In a particular embodiment, the cancer is selected from the group consisting of breast cancer, colorectal cancer, renal carcinoma, prostate cancer, melanoma, and lymphoma, and lung cancer, for example non-small cell lung cancer.

FIGURE LEGENDS

FIG. 4 TLR7 and 8 induce survival of lung tumor cells. (A) A549 cells were unstimulated, stimulated with loxoribine (10 μg/ml), Poly U (10 μg/ml), or Gardiquimod(10μg/ml) and incubated with Alamar blue for 10 days. Reduction of Alamar blue was then determined by spectrophotometry at 570 and 600 nm. The percentage of reduced Alamar blue was calculated as described by the manufacturer. A549 cells were unstimulated or stimulated with loxoribine, Poly U, Gardiquimod, etoposide, or cycloheximide for 24 h. (B) The percentage of dead cells was determined by Trypan blue exclusion. (C) The DNA content was measured by IP staining after RNAse A treatment. The percentages indicate the proportion of subdiploid (G0/G1) and diploid cells (G2/M). Data represent mean values±SD from 3 independent experiments ($*p<0.05$; $** p<0.01$, Student test). (D) A549 cells were cultured for 6 h in the presence of loxoribine, Poly U, or Gardiquimod, and the expression of Bcl-2 was assayed using Taq Man Low Density Array technology. The $\Delta CT$ values for Bcl-2 expression were calculated by subtraction of the CT value obtained for the 18S housekeeping gene. The $\Delta\Delta CT$ values were obtained by subtraction of $\Delta CT$ values for unstimulated cells from those obtained for stimulated cells. The fold increase (arbitrary unit) was obtained by $2^{-\Delta\Delta CT}$.

FIG. 7 Top 10 genes modulated by TLR7 and 8 in human primary lung cancer cells. Total RNA was extracted from primary tumor cells (3 adenocarcinoma: patients P33, P84, P97, and 3 squamous cell carcinoma: patients P23, P25, P31) or SK-MES and A549 cells stimulated with loxoribine, Poly U, or Gardiquimod, and the expression of 182 genes was assayed using Taq Man Low Density Array technology after retrotranscription. All genes with a CT value greater than 35CT were excluded from the analysis. The $\Delta CT$ values for gene expression were calculated by subtraction of the CT value of the 18S housekeeping gene. The $\Delta\Delta CT$ values were obtained by subtraction of the $\Delta CT$ values for unstimulated cell lines from those obtained for primary tumor cells or TLR7- or 8-stimulated cell lines. Values were then clustered using the Genesis software. To compare stimulated cell lines and human primary lung cancer cells, the 10 genes that were highly modulated in FIG. 6 were compared.

EXAMPLES

Example 1

Materials and Methods
Patient Tumors
Human primary lung tumor tissues were obtained from the Institut Mutualiste Montsouris (Paris, France) after medical surgery of stage I to III tumor patients (TNM classification). All patients underwent complete surgical resection of their tumors, including multilevel lymph node sampling or lymphadenectomy, but none received pre-operative chemotherapy or radiotherapy. Patients with mixed histologic features, metastasis, or pleural invasion were ineligible. The consent of all patients was obtained even though French law does not require specific approval of an Institutional Review Board or the consent of patients for retrospective observational, non-interventional analysis of medical records.

NSCLC Cell Lines
The A549 and Adenocarcinoma (ADC) cell lines and SK-MES Squamous Cell Carcinoma (SCC) were obtained from the American Type Culture Collection (ATCC). The H1355 ADC cell line was obtained from Dr. S. Rogers (Brigham and Women's Hospital, Boston, Mass.). All cell lines were cultured in DMEM/F12 medium (Invitrogen, Cergy Pontoise, France) containing 10% heat-inactivated FCS, 1% Ultroser G, and 1% penicillin-streptomycin (Life Technologies, Cergy Pontoise, France) at 37° C. in a humidified atmosphere with 5% $CO_2$.

RNA Isolation and Reverse Transcription-PCR
Total RNA was isolated from lung tumor cell lines or from freshly purified human lung cancer cells using the Qiagen RNeasy kit, and the quality of the extracted RNA was determined by BioAnalyser 2100 array (Agilent, Massy, France). Retrotranscription was performed using 1 µg of RNA (Applied Biosystem, Courtaboeuf, France), and PCR to amplify TLR1 to 10 was performed using primers designed by Invivogen (Toulouse, France).

Flow Cytometry
The A549, H1355, or SK-MES tumor cells were fixed with 1% paraformaldehyde in PBS and permeabilized in PBS buffer containing 0.1% saponin (Sigma, La Verpilliere, France) and 2% FCS. Cells were stained with polyclonal anti-TLR7 or monoclonal PE-conjugated anti-TLR8 (clone 44C143) antibodies (Alexis, Grünberg, Germany). Staining was assessed with a FACScalibur cytometer, and flow cytometry data were analyzed using Cellquest Pro software (BD Biosciences, Le Pont-De-Claix, France).

Immunohistochemistry
Paraffin-embedded tumor biopsies with representative areas of tumor and adjacent lung parenchyma were retrieved retrospectively from 13 patients diagnosed with early-stage NSCLC. The expression and subcellular localization of TLR7 and 8 by tumor cells, bronchial cells, and immune cells was performed as follows: serial 5 µm tissue sections were deparaffinized, rehydrated, and pretreated in 10 mM citrate buffer, pH 6 for antigen retrieval. Sections were incubated with $H_2O_2$ for 15 min, and then blocked in 5% human serum for 30 min at room temperature. Samples were incubated with either polyclonal anti-TLR7 or monoclonal anti-TLR8 antibody (Alexis) for 1 h at room temperature. Control isotype antibodies served as negative controls. Specific staining was detected by incubation with either Envision rabbit or mouse HRP (Dako Cytomation, Trappes, France) for 30 min, followed by a 5 min incubation with 3-amino-9-ethylcarbazole (AEC) substrate (Vector Laboratoires, Burningame, USA). Tissue sections were then counterstained with Harry's hematoxylin (Sigma), and slides were mounted with Glycergel Mounting Medium (Dako Cytomation, Trappes, France) and visualized by light microscopy (Leica Axiovert II, Rueil-Malmaison, France).

Western Blot Analysis
A549 cells ($1.10^6$ cells) were starved for 4 hours in medium containing 2% FCS, and then stimulated with loxoribine, PolyU, or TNFα (10 ng/ml) for different periods of time as indicated. Cells were lysed in 50 mM Tris-HCl, pH 7.5, 150 mM NaCl, 2 mM EDTA, 0.5% triton X100, 2 mM Na$_3$VO$_4$, 10 mM NaF, and 10 mM sodium pyrophosphate supplemented with a complete protease inhibitor cocktail (Boehringer, Paris, France). Protein contents in the cell lysates were quantified using the quick start Bradford protein assay kit (Biorad, Marnes-La-Coquette, France) to ensure that all samples contained similar amounts of protein. Proteins (30 µg) were resolved in 10% Tris-glycine polyacrylamide gels (Invitrogen, Cergy Pontoise, France) and transferred to PVDF immobilon-P membranes (Millipore, Molsheim, France). Blots were probed with monoclonal antibody against phospho-IκBα (Cell Signaling Technology, Danvers, USA), total IκBα, and actin (Santa Cruz, Le Perray en Yvelines, France).

Tumor Cell Proliferation Assay

Human lung cancer cell lines were seeded in 96-well plates (800 cells per well) and left unstimulated or were stimulated with loxoribine, Poly U, or Gardiquimod. The proliferation assay was performed with Alamar blue (AbD Serotec, Cergy Pontoise, France) according to the manufacturer's instructions. Briefly, cells were seeded and stimulated with TLR ligands in 100 µl of medium, and 10 µl of Alamar Blue was added. The optical density in each well was determined at 540 nm and 570 nm after 10 days of culture, and the percentage of reduced Alamar blue was determined. The percentage of reduced Alamar blue in unstimulated cells was determined as 100%, and the percentages of the stimulated cells were determined relative to this value.

Chemoresistance Assay

A549 and SK-MES cells were seeded in 96-well plates (1000 cells per well) and left unstimulated or were stimulated with loxoribine, Poly U, or Gardiquimod for 48 h. Cisplatine, carboplatine, doxorubicine, Navelbine, or cycloheximide was then added for an additional 36 h. The optical density in each well was determined 24 h after the addition of Alamar blue at 540 nm and 570 nm. Alternatively, viable and dead cells were counted using Trypan blue.

Alternatively, chemoresistance was assessed by the colony formation assay. In this assay, 1549, H1355 and SK-MES cells were seeded in 6-well plates (500 cells per well) and incubated for 15 days at 37° under 5% CO$_2$. The cells were left unstimulated or stimulated 100 µM Loxoribine or with 10 µg/ml single-stranded polyU RNA (InvivoGen) on days 0, 3, 6 and 9. On day 12, different anti-cancer agents were added at the respective LD50 (cisplatin and carboplatin 100 µM, navelbine 50 µM, doxorubicine 2 nM). On day 15, the wells ware washed with PBS, and stained with 6% (vol/vol) glutaraldehyde, 0.5% (wt/vol) crystal violet in water for 30 minutes. The cells were washed and the colonies of more than 50 cells counted. Cell survival was calculated as follows: number of colonies after chemotherapy/number of cells seeded on day 0×plating efficiency, where the plating efficiency is number of colonies/number of cells seeded.

Cell Cycle Analysis

A549 cells were cultured in the presence of loxoribine, Poly U, Gardiquimod, etoposide, or cycloheximide. After 48 h, the cells were harvested, washed in cold PBS, and fixed with 2 ml of 70% cold ethanol in PBS for 2 h at 4° C. After centrifugation, the supernatant was removed and the pellet was rinsed with 0.5% PBS Tween. It was then incubated with 50 µh of RNAse A and 50 µg of propidium iodide in PBS. Propidium iodide staining was determined with a FACScalibur cytometer.

Purification of Primary Lung Tumor Cells

Tumoral tissues, obtained after surgery, were mechanically dilacerated, and single cell suspensions were obtained after digestion with collagenase A (1 mg/ml) and DNAse (100 IU/ml) (Sigma-Aldrich) for 1 h at 37° C. under magnetic agitation in serum free RPMI1640, as previously described. Cells were incubated with anti-Epithelial Membrane Antigen (EMA), anti-EpCam (clone BrEp4), and anti-cytokeratin (clone AE1-AE3) monoclonal antibodies (BD Biosciences) for 20 min at 4° C. Labeled cells were then incubated with microbeads coupled to goat anti-mouse antibody. Tumor cells expressing EMA, BrEP4, and AE1-AE3 were then sorted by magnetic isolation according to the instructions of the manufacturer (Miltenyi Biotech, Paris, France). The purity, as determined by flow cytometry, was greater than 90%.

Transcriptomic Analysis

Total RNA was extracted from A549 or SK-MES cells stimulated with loxoribine, Poly U, or Gardiquimod for 6 h or from purified human lung cancer cells using the RNeasy isolation-kit RNA (Qiagen, Courtaboeuf, France). The integrity and the quantity of the RNA were evaluated with a bioanalyzer-2100 (Agilent Technologies). All samples were assessed for gene expression analysis using the Taq Man Low-Density Array angiogenesis and immune panel (Applied Biosystem). The RT-PCR experiments were carried-out according to the manufacturer's instructions (Applied-Biosystems). Quantitative real-time TaqMan-PCR was performed using Low-Density-Arrays and the 7900 robotic real-time PCR-system (Applied-Biosystems). The 18S primers and probes were used as internal controls. Data were analyzed using the SDS Software v2.2 (Applied-Biosystems). The ΔCT values were calculated for each gene by subtraction of the CT value of the 18S housekeeping gene from the CT of the gene of interest. The ΔΔCT values were obtained by subtraction of the ΔCT values for unstimulated cells from the CT obtained for stimulated cells. The fold increase (arbitrary unit) was obtained by $2^{-\Delta\Delta CT}$. Average-linkage hierarchical clustering was applied, and the results were displayed using the GENESIS program (software available online (e.g., at Graz University of Technology website) in order to perform Pearson un-centered hierarchical clustering.

Results

TLR7 and TLR8 are Expressed in Human Lung Tumors

Figure 1:
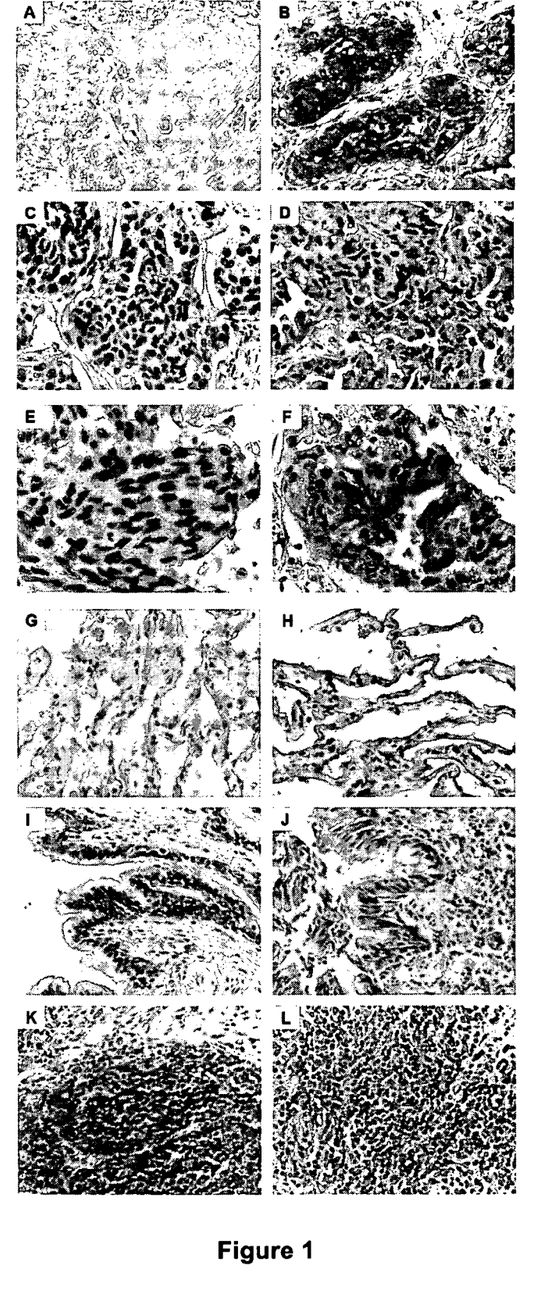
FIG. 1 TLR7 and 8 are expressed in human lung tumors. TLR7 (A, C, E, G, I, K) and TLR8 (B, D, F, H, J, L) protein expression was analyzed in the tumoral area ( ) ADC(C-F), and SCC (A, B) in the alveolar epithelium (G, H), bronchial epithelium (I, J), and tumor-induced bronchus-associated lymphoid tissues (K, L) by immunohistochemical labeling of paraffin-embedded lung tumors, as described in the materials and methods (Original magnification, ×40). The subcellular localization of TLR7 and TLR8 was detected in tumor cells at ×65 magnification (E, F).

Detection of TLR7 and TLR8 expression by malignant and non-malignant lung tissues was performed for thirteen patients with adenocarcinoma (ADC) or squamous cell carcinoma (SCC), two types of non small cell lung cancer (NSCLC). We observed that TLR7 was expressed by tumor cells in 70% of the patients tested (Table 1). For example, FIGS. 1A and C show positive tumor cell expression in SCC and ADC, respectively. In contrast, TLR8 was highly expressed by tumor cells in all lung cancer patients tested independent of the histological type (Table 1 and FIGS. 1B, D). Comparison of the precise cellular localization of TLR7 and TLR8 revealed major differences, with TLR7 expression being mainly perinuclear (FIG. 1E) and TLR8 being more diffuse and cytoplasmic (FIG. 1F). Interestingly, no TLR7 or TLR8 expression could be detected in epithelial alveolar cells from the same patients (FIG. 1G, H), whereas strong expression of TLR7 and TLR8 was detected in bronchial epithelial cells, an observation that has never been previously described (FIG. 1I, J). This observation suggests that the expression of TLR7 or TLR8 is acquired during or upon initiation of the tumoral process. It is reported that immune cells, including NK, plasmacytoid and myeloid dendritic cells, and B and T lymphocytes can express TLR7 and/or TLR8. Immune cell infiltration has been described in lung tumors. In some patients, the immune cells are organized into lymphoid-like structures called tumor-induced bronchus-associated lymphoid tissues (TiBALT) (55). Accordingly, we observed that most of the immune cells present in the TiBALT strongly express TLR7 (FIG. 1K), whereas fewer cells express TLR8 (FIG. 1L). Moreover, we also observed the presence of TLR7-positive immune cells outside of the TiBALT (data not shown). These observations demonstrate distinct profiles of TLR7 and 8 expression; TLR7 is expressed by immune and bronchial cells and, in 70% of the patients, in tumoral cells, whereas TLR8 is mainly expressed by bronchial and tumoral cells.

TLR7 or 8 Stimulation Induces Survival of Lung Cancer Cell Lines

We examined whether TLR7 or 8 stimulation of lung tumor cells could increase the proliferation of A549 cells. We observed that stimulation with loxoribine, Poly U, or Gardiquimod (heterodimeric TLR7/8 ligand) for ten days induced a significant increase in cell proliferation and/or viability as compared to unstimulated cells since the reduc-

TABLE 1

TLR7 and 8 expression in the lung tumor and microenvironment.

| Patient | Histologic type | pTNM | TLR7 Tumor cells | TLR7 Bronchial cells | TLR7 BALT | TLR8 Tumor cells | TLR8 Bronchial cells | TLR8 BALT |
|---|---|---|---|---|---|---|---|---|
| #1 | ADC | T1N0M0 | +++ | +++ | + | +++ | +++ | + |
| #2 | ADC | T1N0M0 | − | +++ | +++ | + | + | − |
| #3 | ADC | T1N + M0 | − | +++ | + | +++ | +++ | + |
| #4 | ADC | T2N0M0 | ++ | + | ++ | +++ | +++ | +++ |
| #5 | ADC | T2N0M0 | + | +++ | ++ | +++ | +++ | + |
| #6 | ADC | T2N0M0 | +++ | +++ | +++ | +++ | + | + |
| #7 | ADC | T2N2M0 | + | +++ | Ø | + | ++ | Ø |
| #8 | ADC | T1N2M0 | ++ | ++ | +++ | +++ | +++ | + |
| #9 | SCC | T2N0M0 | − | +++ | +++ | +++ | − | + |
| #10 | SCC | T2N0M0 | − | + | +++ | +++ | + | ++ |
| #11 | SCC | T2N1M0 | +++ | +++ | +++ | ++ | − | ++ |
| #12 | SCC | T2N2M0 | + | ++ | +++ | +++ | ++ | + |
| #13 | SCC | T3N0M0 | + | +++ | ++ | +++ | + | + |

TLR7 and 8 expression was determined in NSCLC lung tumors, either in ADC or in SCC.
The numbers indicate the results of a semi-quantitative analysis of positivity.
−: no detectable expression,
+: less than 30% TLR expressing cells,
++: 30-60% TLR expressing cells, and
+++: 60-100% TLR expressing cells.
Ø: No BALT.

TLRs are Expressed by Human Lung Cancer Cell Lines

Figure 2:
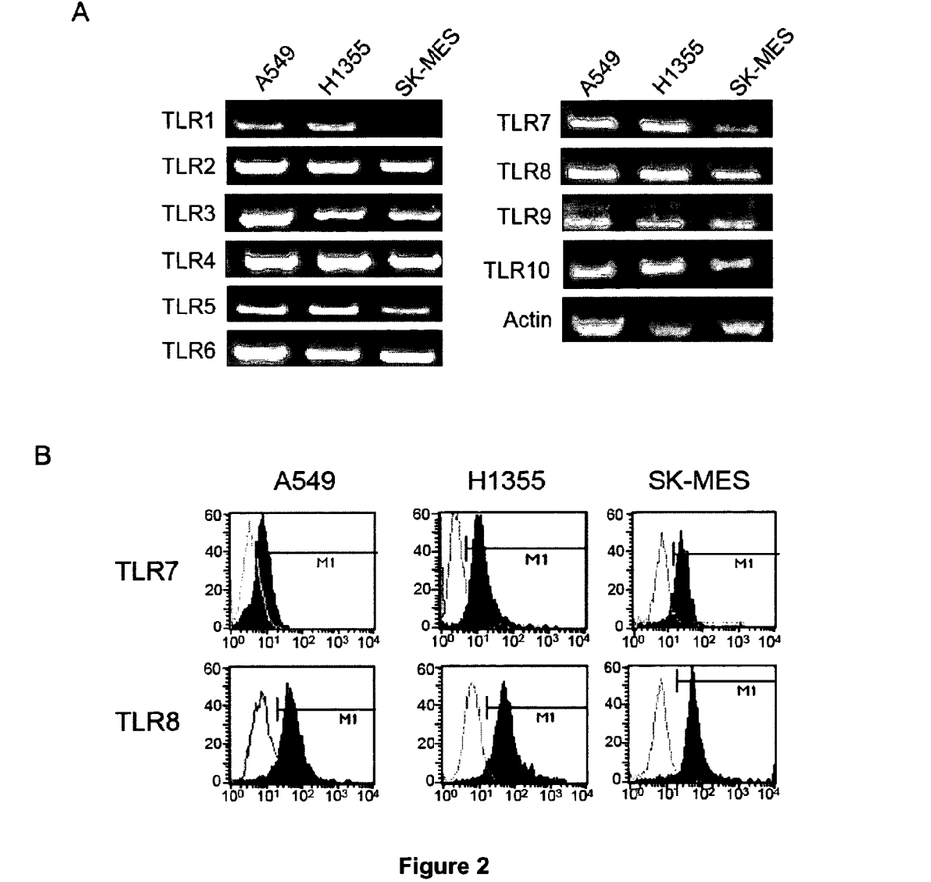
FIG. 2 Human lung cancer cell lines express TLRs. (A) Expression of TLR1 to 10 in A549, H1355, and SK-MES cell lines were analyzed by RT-PCR. One representative of three independent experiments is presented. (B) Expression of TLR7 and 8 was determined in the cells by flow cytometry after intracellular staining. Results are representative of three independent experiments. Gray histograms represent isotype controls and black histograms represent TLR7 or TLR8 Abs.

We characterized the expression of TLRs in several human lung tumor cell lines including A549, H1355 (ADC), and SK-MES (SCC). All tumor cell lines expressed TLR1 to 10 (FIG. 2A), and the expression of TLR7 and 8 was confirmed at the protein level by flow cytometry analysis (FIG. 2B) and immunohistochemistry (data not shown).

Figure 3:
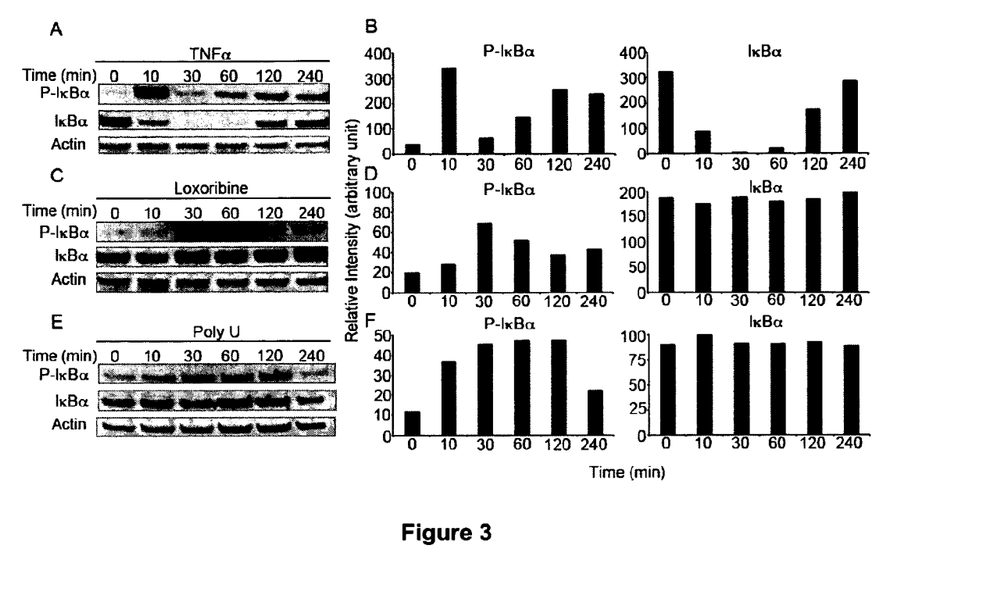
FIG. 3 TLR7 and TLR8 lead to IκBα phosphorylation, but not degradation. A549 cells were untreated or treated with TNF-α (10 ng/ml) (A, B), loxoribine (10 μg/ml) (C, D), or Poly U (10 μg/ml) (E, F) for the indicated periods of time. The cell lysates were analyzed by immunoblot with anti-phospho-specific IκBα, anti-IκBα and anti-actin antibodies (A, C, E). Quantification of the bands was realized using Image J software (B, D, F). Histograms represent the intensity of each band observed in the blots at the indicated time point and are expressed in arbitrary units normalized to actin intensity (relative intensity) both for phospho-IκBα and IκBα. Results are representative of three independent experiments.
Figure 4:
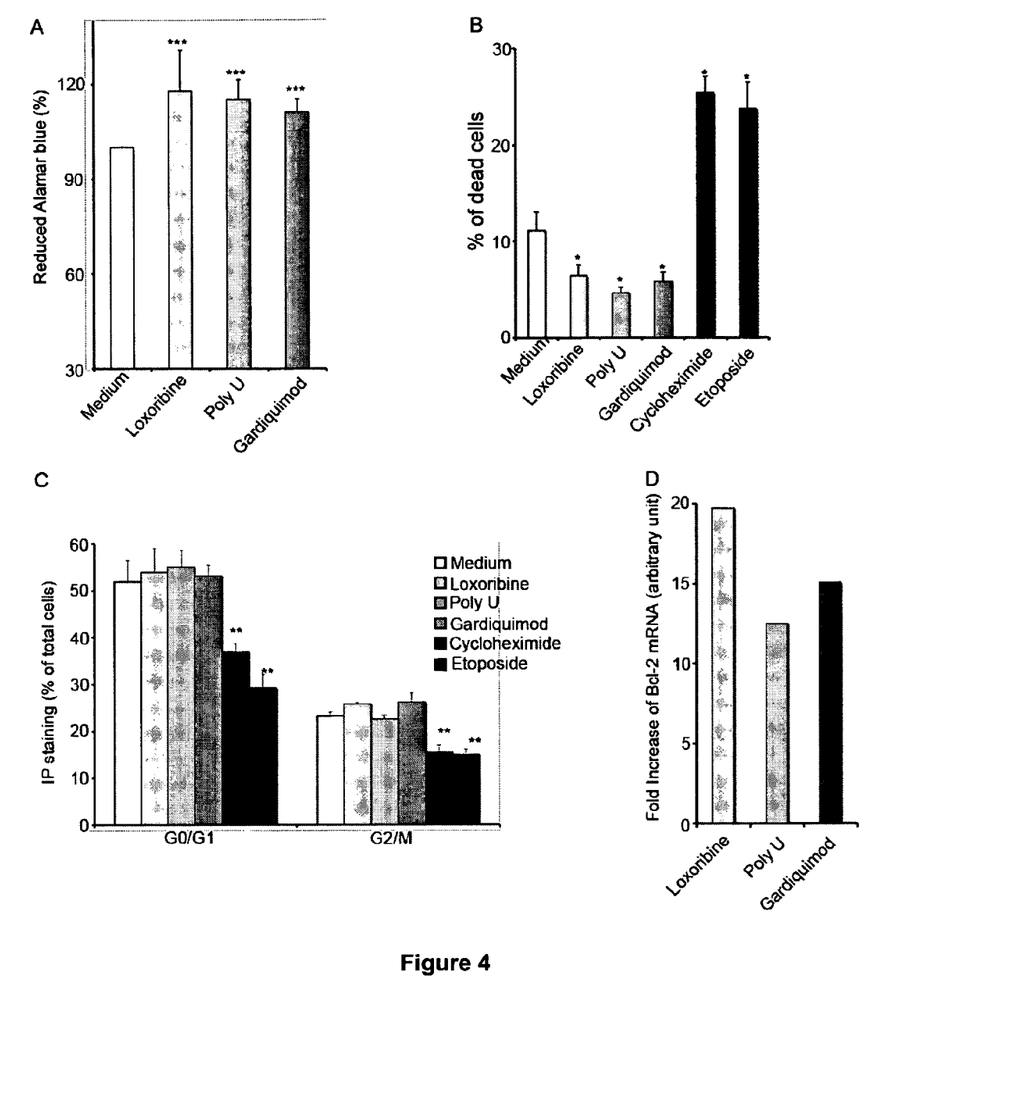

TLR7 or 8 Stimulation of Human Lung Cancer Cell Lines Induces Atypical NFκB Activation In order to determine if the TLR7 and 8 expressed by lung tumor cell lines were able to induce intracellular signaling pathways, we studied NF-κB activation in response to stimulation with TNFα, loxoribine (homodimeric TLR7 ligand), or Poly U (homodimeric TLR8 ligand). As expected, we observed that TNFα stimulation induced canonical activation of NF-κB, as revealed by IκBα phosphorylation and degradation (FIG. 3A, B). In contrast TLR7 or 8 stimulation led to atypical NF-κB activation. In response to loxoribine or Poly U, IκBα was phosphorylated in thirty minutes, but was not degraded (FIG. 3C-F). Furthermore, we also observed that the kinetics of IκBα phosphorylation were dependent on the stimulus. On the one hand, TNFα stimulation induced two waves of IκBα phosphorylation; the first one after ten minutes was associated with IκBα degradation, and the second one after sixty minutes was not associated with IκBα degradation. On the other hand, we observed that TLR stimulation induced only a phosphorylation of IκBα, with a maximum phosphorylation obtained after thirty minutes without degradation of IκBα. These results indicate that TLR7 and 8, which are expressed by human lung cancer cell lines, induce NFκB activation, and suggest that TLR7/8 and TNFα might mediate differential signaling pathways leading to NF-κB activation, as was recently described by Qin J. et al (37).

tion of Alamar blue was increased by 20% in stimulated cells (FIG. 4A). This effect could be attributed to either protection against cell death or modification of the cell cycle. Therefore, we analyzed the effects of TLR7 or TLR8 stimulation on cell death, and observed that treatment with loxorine, Poly U, or Gardiquimod induced a 1.5- to 2-fold decrease in the percentage of dead cells compared with unstimulated cells. Treatment with cycloheximide or etoposide, which were used as positive controls, led to a significant 2.5-fold increase in the percentage of dead cells (FIG. 4B). Finally, we determined the proportion of cells in the G0/G1 or G2/M phases of the cell cycle in response to TLR7 or 8 stimulation. We did not observe any significant differences between unstimulated and stimulated cells for the G0/G1 or G2/M phases, whereas etoposide or cycloheximide treatment resulted in a significant reduction in the percentage of cells in G0/G1 or G2/M (FIG. 4C). These results are consistent with the increased expression of Bcl-2 in A549 cells observed by RT-PCR analysis in response to stimulation by loxoribine, Poly U, or Gardiquimod compared to untreated cells (FIG. 4D). Similar results were obtained in SCC SK-MES cells, which demonstrated a 100-fold increase in Bcl-2 expression (data not shown).

The results suggest that TLR7 or 8 stimulation induced a pro-survival rather than a proliferative effect.

Altogether, the results demonstrate that treatment with an agonist of TLR7 or an agonist of TLR8 promotes tumor cell survival.

TLR7 or 8 Stimulation Induces Chemoresistance in Lung Cancer Cell Lines

Figure 5:
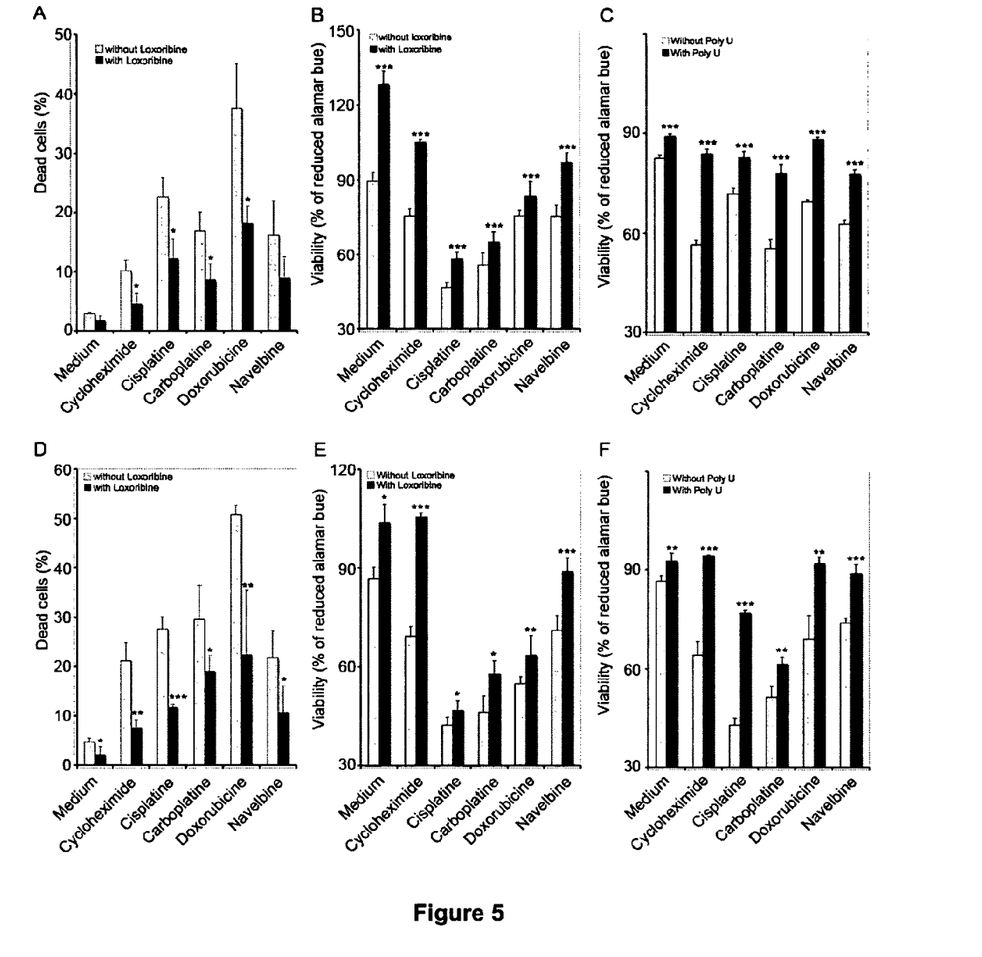
FIG. 5 TLR7 and 8 induce chemoresistance of lung tumor cells. A549 (A-C) or SK-MES cells (D-F) were cultured with or without loxoribine or Poly U for 48 h, and then left untreated or were treated with cycloheximide, cisplatine, carboplatine, doxorubicine, or Navelbine. After 36 h, the percentage of dead cells was determined by Trypan blue exclusion (A, D) and cell viability was analyzed by the reduction of Alamar blue (B, C, E and F). Data represent mean values±SD from 3 independent experiments ($*p<0.05$; $p<0.01$, $*p<0.001$, Student test).

Chemotherapy is frequently used as a neo-adjuvant treatment for lung cancer (40). Having observed that TLR7 or 8 stimulation could increase tumor cell viability and Bcl-2 expression, we hypothesized that it could interfere with the induction of apoptosis caused by chemotherapy. Therefore, we analyzed the induction of cell death by chemotherapeutic agents currently used for the treatment of Non-Small-Cell Lung Cancer (NSCLC) in A549 or SK-MES cells previously stimulated with loxoribine or Poly U. We observed that treatment with cycloheximide, cisplatine, carboplatine, doxorubicine, or Navelbine induced A549 and SK-MES cell death, with percentages of trypan blue positive cells ranging from 10 to 40% depending on the drug used (FIG. 5A, D). Interestingly, when the cells were stimulated with loxoribine prior to treatment with chemotherapeutic agents, cell death was reduced by about two fold (FIG. 5A, D). Consistent with this observation, we also analyzed the survival of tumor cells conferred by loxoribine or poly U prior to treatment with chemotherapeutic agents by the Alamar Blue reduction assay. Chemotherapy induced a reduction in cell viability both in A549 (FIG. 5B, C) and SK-MES cells (FIG. 5E, F). This depended on the drug used, with cisplatine and carboplatine being more potent inducers of cell death. Stimulation of the cells with either loxoribine (FIG. 5B, E) or Poly U (FIG. 5C, F) prior to induction of apoptosis resulted in significantly higher viability, demonstrating that tumoral cells are less sensitive to chemotherapy-induced cell death.

Taken together, these results indicate that stimulation of tumor cell lines, with either TLR7 or TLR8 ligands, induces chemoresistance and protect tumor cells against apoptosis by a mechanism that may involve Bcl-2.

The effect on combined chemotherapy was also studied. Combination of several anti-cancer agents induced a stronger decrease in the number of un-stimulated colonies compared to the same agents used in monotherapy. When the cells were stimulated with Loxoribine and/or with polyU, they were more resistant to treatment with combined anti-cancer agents.

Therefore, stimulation with a TLR7 agonist or a TLR8 agonist induces, not only chemoresistance to single anti-cancer agents, but also to combined anti-cancer agents typically used in polychemotherapy.

TLR7 or 8 Stimulation Modulates Gene Transcription

Figure 6:
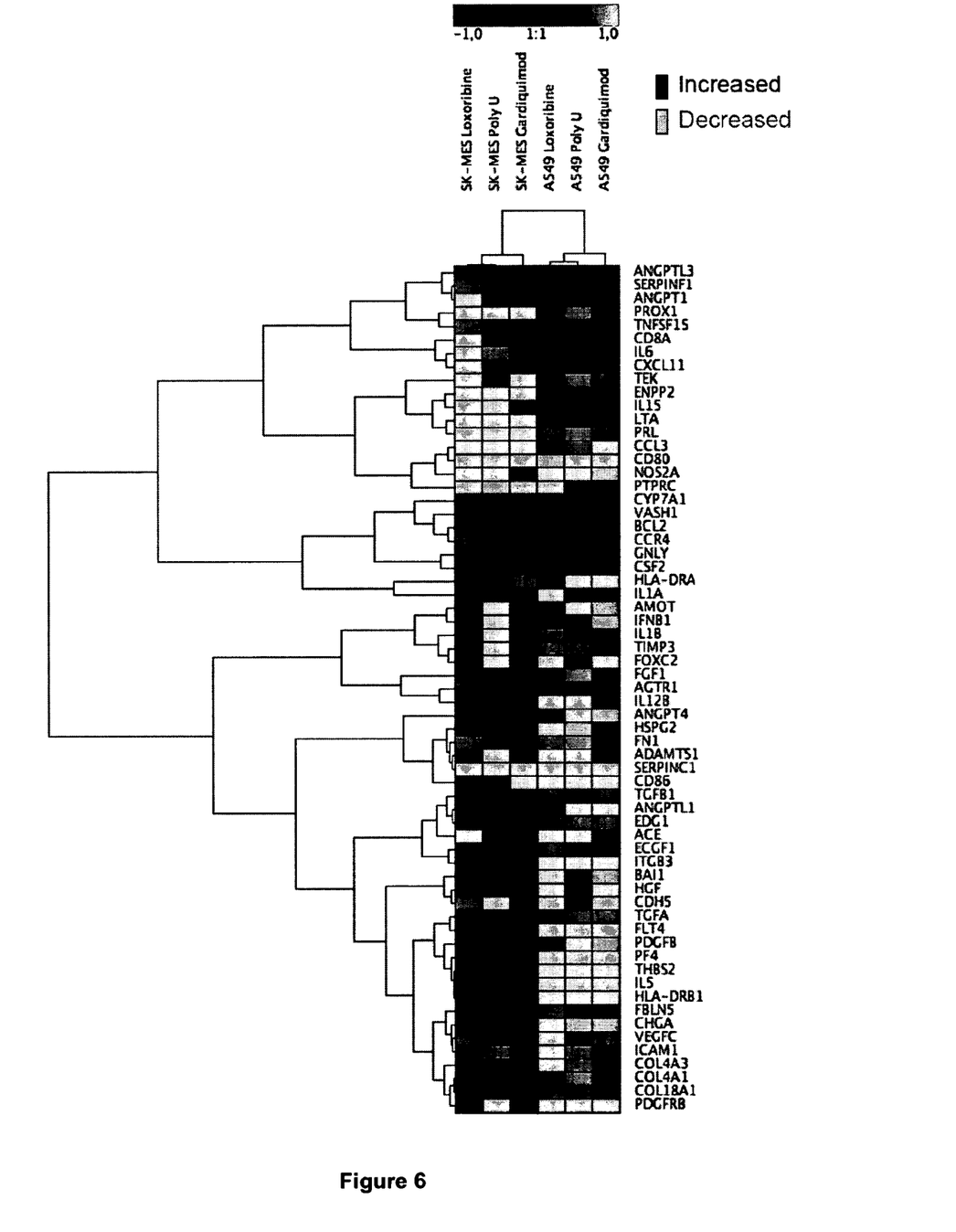
FIG. 6 TLR7 and 8 induce regulation of gene transcription. A549 or SK-MES cells were cultured for 6 h in the presence of loxoribine, Poly U, or Gardiquimod. Total RNA was extracted and analyzed for the expression of 182 genes using Taq Man Low Density Array technology. All genes with a value greater than 35 (CT) were excluded from the analysis. The $\Delta CT$ values for the expression of all genes were calculated by subtraction of the CT value of the 18S housekeeping gene. The $\Delta\Delta CT$ values were obtained by subtraction of the $\Delta CT$ values for unstimulated cells from those obtained for TLR7- or 8-stimulated cells. The fold increase (arbitrary unit) was obtained by $2^{-\Delta\Delta CT}$. Values were then clustered using the Genesis Software.

In immune cells, TLR stimulation leads to up-regulation of pro-inflammatory cytokines However, there is little information available regarding the molecules that are modulated when tumoral cells are stimulated with TLR ligands. Therefore, we analyzed the modulation of gene expression in A549 and SK-MES cells in response to TLR7 or 8 stimulation by screening a large panel of immune and angiogenic genes. To this end, cells were stimulated with loxoribine, Poly U, or Gardiquimod, and the expression of 182 RNAs by TaqMan Low Density array was analyzed. The ΔΔCT values were obtained by comparison of unstimulated cells with cells stimulated by loxoribine, Poly U, or Gardiquimod. We analyzed the global profile of genes that are modulated by clustering methods using the Genesis software and the Pearson Uncentered algorithm. Here, we have clustered the 60 genes that were most differentially modulated in TLR7- or 8-stimulated cells in comparison to unstimulated cells (FIG. 6). TLR stimulation induced the up-regulation of Bcl-2, CCR4, and Vasohibin-1 (VASH-1) and down-regulation of Prolactin (PRL), CD80, Fibronectin-1 (FN-1), A Disintegrin And Metalloproteinase with ThromboSpondin motif 1 (ADAMTS1), and Serpin Peptidase Inhibitor Clade C1 (SERPINC1) in both SK-MES or A549 cells. Interestingly, we also observed some genes that were specifically modulated depending on the histological origin of the cell line, with Angiopoietin like 3 (ANGPTL3), Serpin Peptidase Inhibitor Clade F1 (SERPINF1), and Angiopoietin 1 (ANGPT1) up-regulated in A549 cells, but down-regulated in SK-MES cells, and ANGPTL1, Platelet Factor 4 (PF4), and fms related tyrosine kinase 4 (FLT4) up-regulated in SK-MES, but down-regulated in A549 cells. These results show that TLR7 and 8 stimulation of lung tumor cells modulates the transcription of a number of genes implicated in several functions including cell survival, angiogenesis, and immune escape.

Figure 7:
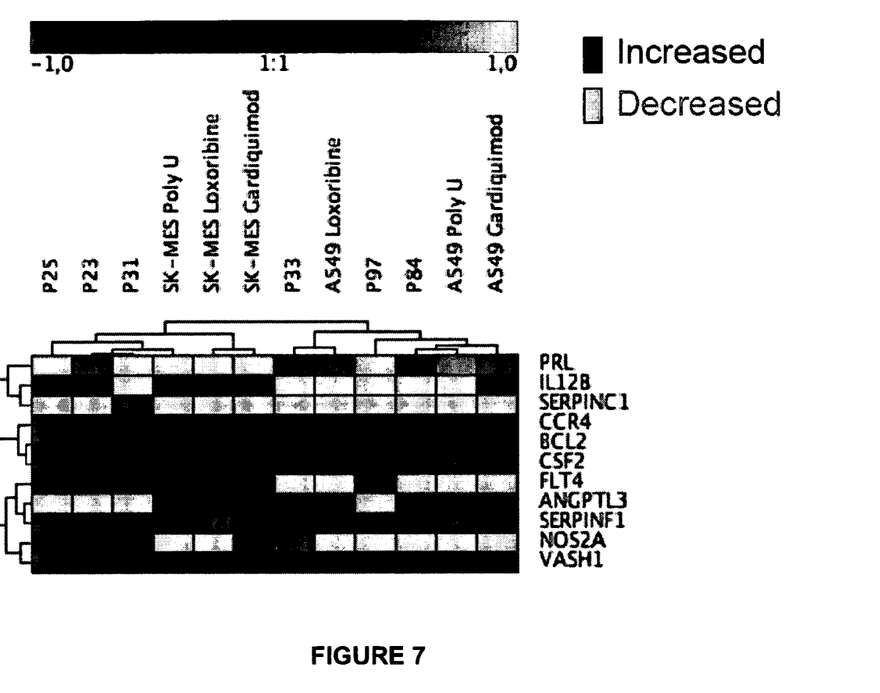

Human Primary Tumor Cells and TLR7- or 8-Stimulated Cell Lines have the Same Gene Expression Profile In order to determine if primary human lung tumor cells that can express high levels of TLR7 or 8 display gene expression profiles similar to TLR7- or 8-stimulated cell lines, we analyzed the same 182 RNAs using the TaqMan Low density array in tumor cells obtained from fresh surgical tissues. The ΔΔCT values were obtained by comparison of unstimulated A549 cells with primary ADC tumor cells or unstimulated SK-MES cells with primary SCC tumor cells. Interestingly, we observed that the profile of ADC is similar to the profile of stimulated A549 and the profile of SCC is similar to that of stimulated SK-MES. We compared the expression levels of the eleven genes that were most differentially expressed by the tumor cell lines. Bcl-2, VASH-1, and CCR4 were always up-regulated in stimulated cell lines and primary human cells, whereas SERPINC1 was always down-regulated (FIG. 7). Moreover, some genes that were differentially expressed between A549 and SK-MES cells were also differentially expressed in primary tumor cells in a similar way. For example, ANGPTL-3 was down-regulated in SK-MES and the three SCC primary tumor cells (P23, P25 and P31), but was up-regulated in A549 and ADC primary tumor cells (P33, P84). The same was observed for other genes such as IL12, NOS2A, and FLT4. This effect was independent of histological type since the results were compared with unstimulated cell lines for each histological origin, which were used as a reference. As a consequence, this clustering of the eleven most differentially expressed genes suggested that primary lung tumor cells might have been stimulated in vivo within the tumor by agonist ligands for TLR7 or 8.

In conclusion, the inventors have demonstrated that agonists of TLR 7 and agonists of TLR8 increase tumor cell survival through Bcl-2 expression and confer resistance to apoptosis induced by chemotherapeutic agents that are currently used to cure cancer patients.

Thus, the inventors show that determining whether cancer cells of a patient suffering from cancer express TLR7 or TLR8 is important for predicting the response to a treatment with an agonist TLR7 or agonist of TLR8 respectively and provide a method for treating cancer comprising the step of determining whether cancer cells of said patient express TLR7 or TLR8.

Example 2

The inventors have obtained biopsies from NSCLC patients (stage IIIA or IV) that have been treated with chemotherapeutic agents, including cisplatin and gemzar. TLR7 and TLR8 expression is studied by immunohistochemistry on these biopsies in order to analyze the correlation between TLR7 or TLR8 expression on tumor cells in the biopsy and the clinical status of the patients after the chemotherapy. Indeed, some patients respond well to the treatment, whereas others are resistant.

The same study is performed on patients having a large B cell lymphoma, on a, cohort of 24 patients, that were included in a protocol of chemotherapy, and for which the clinical status after the therapy is known.

Preliminary results indicate that, as for NSCLC patients, the expression on TLR7 in the tumors is heterogeneous. Indeed:
- in 9 patients out of 24, 100% of the tumor cells were TLR7+;
- in 9 patients out of 24, 50% of the tumor cells were TLR7+;
- in 1 patient out of 24, 25% of the tumor cells were TLR7+;
- in 5 patients out of 24, 0% of the tumor cells were TLR7+.

Example 3

In this example, the inventors have demonstrated that the expression of TRL7 in cancer cells is a good indicator for predicting the response to treatment with an anti-cancer agent in a patient suffering from cancer. They also demonstrate that the expression of TLR7 in cancer cells is correlated with the development of metastatic tumors and with poor prognosis.

NOD/SCID Mice
Material and Methods

NOD/SCID (nonobese diabetic/severely compromised immunodeficient) mice were bred at the animal facility of the Centre de Recherche des Cordeliers, Paris, France, from NOD/SCID parents obtained from Charles River (France). Mice were anesthetized by intra-peritoneal injection of a solution containing 3.2 mg of ketamine (Virbac) and 0.16 mg of xylasine (Rompum 2%, Bayer Healthcare) in 80 µl of PBS (Gibco). Five days prior to experimentation, A549 cells were pre-stimulated with 100 µM Loxoribine (Invivogen) or left unstimulated. For each condition $5\times10^6$ cells were diluted in 250 µl PBS and injected subcutaneously to 5 mice per group and were re-stimulated either with 50 µl PBS or with 100 nmol of Loxoribine diluted in 50 µl PBS. Stimulating injections into the tumor site were carried out on the day the cells were injected and then on days 3, 6 and 9. The mice then received either 120 µA PBS, or a chemotherapy of cisplatine (2 mg/kg/injection diluted in 120 µl PBS) on days 18, 20 and 22, both intra-peritoneal. The volume of the tumor was determined by measuring the length (Lg), the width (Wi) of the tumor and by calculating (Lg*(Wi*Wi)/2.

Results

NOD/SCID mice have a defective immune system and are used for carrying out xenografts of tumor cells of human origin without any graft rejection.

In the control group (NS, receiving non stimulated 1549 cells) the tumor volume increased progressively from week 9 to reach a volume of 4 cm³ by week 14. In contrast, in mice of the Loxoribine group, the tumor volume increased more and reached 8 cm³ by week 14, indicating that the A549 cells proliferate in vivo in the NOD/SCID mice and that Loxoribine induces a greater tumor development. Survival of the mice correlated with tumor growth. Indeed, a 50% mortality was observed towards week 17 in NS mice and towards week 15 in Loxoribine mice. Autopsy showed that the Loxoribine mice had more ganglionic and pulmonary metastases than control mice.

The effect of chemotherapy on tumor growth was studied by comparing the growth of the tumor in mice that had received cisplatin versus mice receiving PBS. Consistent with the results described above, seven weeks after injection of tumor cells, the tumor volumes were 2.5 times higher in the PBS-treated Loxoribine pre-stimulated group (5.3 cm³) compared to the PBS-treated NS group (1.9 cm³). Chemotherapy in the NS reduced by a factor 3 the size of the tumor (0.6 cm³), demonstrating that chemotherapy was effective in vivo. However, in the Loxoribine-stimulated group, the reduction was only by a factor 1.6. The mice of the Loxoribine group were therefore less responsive to treatment with an anti-cancer agent.

NSCLC Patients

Sections of metastatic ganglia were obtained from 23 NSCLC patients before neo-adjuvant chemotherapy. The proportion of cells expressing TLR7 was estimated in a semi-quantitative manner by immunohistochemistry.

Interestingly, two clear groups of patients could be distinguished: group "A" in which the ganglia were infiltrated at more than 70% by tumor cells expressing TLR7, and group "B" in which the ganglia were infiltrated by tumor cells expressing TLR7 at less than 30%.

The inventors observed that:
- 8 out of 12 patients of group A were non-responders to chemotherapy,
- 8 out of 11 patients f group B were responders to chemotherapy.

This correlation evidences that the expression of TRL7 in cancer cells can be used to predict response to treatment, wherein expression of TLR7 in cancer cells is indicative of poor response to treatment.

Further, the inventors have investigated, in 19 out of the 24 patients of the present study, whether the expression of TRL7 was correlated with the development of metastases at a distance after tumor recurrence. The inventors have observed that:
- 8 out 9 patients of group A developed metastases,
- only 4 out of 10 patients of group B developed metastases.

Moreover, the average survival without recurrence of patients of group A was 16 months, compared to 31 months for patients of group B.

References

Throughout this application, various references describe the state of the art to which the invention pertains. The disclosures of these references are hereby incorporated by reference into the present disclosure.

1. Balkwill, F., and Mantovani, A. 2001. Inflammation and cancer: back to Virchow?*Lancet* 357:539-545.
2. Clevers, H. 2004. At the Crossroads of Inflammation and Cancer. *Cell* 118:671-674.
3. Coussens, L. M., and Werb, Z. 2002. Inflammation and cancer. *Nature* 420:860-867.
4. Keller, S. A., Hernandez-Hopkins, D., Vider, J., Ponomarev, V., Hyjek, E., Schattner, E. J., and Cesarman, E. 2006. NF-kappaB is essential for the progression of KSHV- and EBV-infected lymphomas in vivo. *Blood* 107:3295-3302.
5. Littman, A. J., Jackson, L. A., and Vaughan, T. L. 2005. Chlamydia pneumoniae and lung cancer: epidemiologic evidence. *Cancer Epidemiol Biomarkers Prev* 14:773-778.
6. Littman, A. J., Thornquist, M. D., White, E., Jackson, L. A., Goodman, G. E., and Vaughan, T. L. 2004. Prior lung disease and risk of lung cancer in a large prospective study. *Cancer Causes Control* 15:819-827.
7. Littman, A. J., White, E., Jackson, L. A., Thornquist, M. D., Gaydos, C. A., Goodman, G. E., and Vaughan, T. L. 2004. Chlamydia pneumoniae infection and risk of lung cancer. *Cancer Epidemiol Biomarkers Prev* 13:1624-1630.
8. Philip, M., Rowley, D. A., and Schreiber, H. 2004. Inflammation as a tumor promoter in cancer induction. *Semin Cancer Biol* 14:433-439.
9. Balkwill, F. 2006. TNF-alpha in promotion and progression of cancer. *Cancer Metastasis Rev* 25:409-416.
10. Killeen, S. D., Wang, J. H., Andrews, E. J., and Redmond, H. P. 2006. Exploitation of the Toll-like receptor system in cancer: a doubled-edged sword? *Br J Cancer* 95:247-252.

11. Lotze, M. T., Zeh, H. J., Rubartelli, A., Sparvero, L. J., Amoscato, A. A., Washburn, N. R., Devera, M. E., Liang, X., Tör, M., and Billiar, T. 2007. The grateful dead: damage-associated molecular pattern molecules and reduction/oxidation regulate immunity. *Immunol Rev* 220:60-81.

12. Trinchieri, G., and Sher, A. 2007. Cooperation of Toll-like receptor signals in innate immune defense. *Nat Rev Immunol* 7:179-190.

13. Karin, M., and Greten, F. R. 2005. NF-kappaB: linking inflammation and immunity to cancer development and progression. *Nat Rev Immunol* 5:749-759.

14. Pikarsky, E., Porat, R., Stein, I., Abramovitch, R., Amit, S., Kasem, S., Gutkovich-Pyest, E., Urieli-Shoval, S., Galun, E., and Ben-Neriah, Y. 2004. NF-kB functions as a tumour promoter in inflammation-associated cancer. *Nature* 431:461-466.

15. Greten, F. R., Eckmann, L., Greten, T. F., Park, J. M., Li, Z. W., Egan, L. J., Kagnoff, M. F., and Karin, M. 2004. IKKbeta links inflammation and tumorigenesis in a mouse model of colitis-associated cancer. *Cell* 118:285-296.

16. Luo, J. L., Tan, W., Ricono, J. M., Korchynskyi, O., Zhang, M., Gonias, S. L., Cheresh, D. A., and Karin, M. 2007. Nuclear cytokine-activated IKKalpha controls prostate cancer metastasis by repressing Maspin. *Nature* 446:690-694.

17. Karin, M., and Lin, A. 2002. NF-kappaB at the crossroads of life and death. *Nat Immunol* 3:221-227.

18. Luo, J. L., Kamata, H., and Karin, M. 2005. IKK/NF-kappaB signaling: balancing life and death—a new approach to cancer therapy. *J Clin Invest* 115:2625-2632.

19. Chen, Y. C., Giovannucci, E., Kraft, P., Lazarus, R., and Hunter, D. J. 2007. Association between Toll-like receptor gene cluster (TLR6, TLR1, and TLR10) and prostate cancer. *Cancer Epidemiol Biomarkers Prev* 16:1982-1989.

20. Tsan, M. F. 2006. Toll-like receptors, inflammation and cancer. *Semin Cancer Biol* 16:32-37.

21. Chen, Y. C., Giovannucci, E., Lazarus, R., Kraft, P., Ketkar, S., and Hunter, D. J. 2005. Sequence variants of Toll-like receptor 4 and susceptibility to prostate cancer. *Cancer Res* 65:11771-11778.

22. Sun, J., Wiklund, F., Hsu, F. C., Bälter, K., Zheng, S. L., Johansson, J. E., Chang, B., Liu, W., Li, T., Turner, A. R., et al. 2006. Interactions of sequence variants in interleukin-1 receptor-associated kinase4 and the toll-like receptor 6-1-10 gene cluster increase prostate cancer risk. *Cancer Epidemiol Biomarkers Prev* 15:480-485.

23. Rakoff-Nahoum, S., and Medzhitov, R. 2007. Regulation of Spontaneous Intestinal Tumorigenesis Through the Adaptor Protein MyD88. *Science* 317:124-127.

24. Xiao, H., Gulen, M. F., Qin, J., Yao, J., Bulek, K., Kish, D., Altuntas, C. Z., Wald, D., Ma, C., Zhou, H., et al. 2007. The Toll-interleukin-1 receptor member SIGIRR regulates colonic epithelial homeostasis, inflammation, and tumorigenesis. *Immunity* 26:461-475.

25. Huang, B., Zhao, J., Li, H., He, K. L., Chen, Y., Chen, S. H., Mayer, L., Unkeless, J. C., and Xiong, H. 2005. Toll-like receptors on tumor cells facilitate evasion of immune surveillance. *Cancer Research* 65:5009-5014.

26. Salaun, B., Coste, I., Rissoan, M. C., Lebecque, S. J., and Renno, T. 2006. TLR3 can directly trigger apoptosis in human cancer cells. *J Immunol* 176:4894-4901.

27. Huang, B., Zhao, J., Shen, S., Li, H., He, K. L., Shen, G. X., Mayer, L., Unkeless, J., Li, D., Yuan, Y., et al. 2007. *Listeria monocytogenes* promotes tumor growth via tumor cell toll-like receptor 2 signaling. *Cancer Res* 67:4346-4352.

28. Droemann, D., Albrecht, D., Gerdes, J., Ulmer, A. J., Branscheid, D., Vollmer, E., Dalhoff, K., Zabel, P., and Goldmann, T. 2005. Human lung cancer cells express functionally active Toll-like receptor 9. *Respir Res* 6:1.

29. He, W., Liu, Q., Wang, L., Chen, W., Li, N., and Cao, X. 2007. TLR4 signaling promotes immune escape of human lung cancer cells by inducing immunosuppressive cytokines and apoptosis resistance. *Mol Immunol* 44:2850-2859.

30. Salaun, B., Lebecque, S., Matikainen, S., Rimoldi, D., and Romero, P. 2007. Toll-like receptor 3 expressed by melanoma cells as a target for therapy? *Clin Cancer Res* 13:4565-4574.

31. Guillot, L., Medjane, S., Le-Barillec, K., Balloy, V., Danel, C., Chignard, M., and Si-Tahar, M. 2004. Response of human pulmonary epithelial cells to lipopolysaccharide involves Toll-like receptor 4 (TLR4)-dependent signaling pathways: evidence for an intracellular compartmentalization of TLR4. *J Biol Chem* 279:2712-2718.

32. Mayer, A. K., Muehmer, M., Mages, J., Gueinzius, K., Hess, C., Heeg, K., Bals, R., Lang, R., and Dalpke, A. H. 2007. Differential recognition of TLR-dependent microbial ligands in human bronchial epithelial cells. *J Immunol* 178:3134-3142.

33. Ardies, C. M. 2003. Inflammation as cause for scar cancers of the lung. *Integrative cancer therapies* 2:238-246.

34. Pons, J., Sauleda, J., Regueiro, V., Santos, C., López, M., Ferrer, J., Agustí, A. G., and Bengoechea, J. A. 2006. Expression of Toll-like receptor 2 is up-regulated in monocytes from patients with chronic obstructive pulmonary disease. *Respir Res* 7:64.

35. Diebold, S. S., Kaisho, T., Hemmi, H., Akira, S., and Reis e Sousa, C. 2004 Innate antiviral responses by means of TLR7-mediated recognition of single-stranded RNA. *Science* 303:1529-1531.

36. Heil, F., Hemmi, H., Hochrein, H., Ampenberger, F., Kirschning, C., Akira, S., Lipford, G., Wagner, H., and Bauer, S. 2004. Species-specific recognition of single-stranded RNA via toll-like receptor 7 and 8. *Science* 303:1526-1529.

37. Qin, J., Yao, J., Cui, G., Xiao, H., Kim, T. W., Fraczek, J., Wightman, P., Sato, S., Akira, S., Puel, A., et al. 2006. TLR8-mediated NF-kappaB and JNK activation are TAK1-independent and MEKK3-dependent. *J Biol Chem* 281:21013-21021.

38. Jego, G., Bataille, R., Geffroy-Luseau, A., Descamps, G., and Pellat-Deceunynck, C. 2006. Pathogen-associated molecular patterns are growth and survival factors for human myeloma cells through Toll-like receptors. *Leukemia* 20:1130-1137.

39. Kelly, M. G., Alvero, A. B., Chen, R., Silasi, D. A., Abrahams, V. M., Chan, S., Visintin, I., Rutherford, T., and Mor, G. 2006. TLR-4 signaling promotes tumor growth and paclitaxel chemoresistance in ovarian cancer. *Cancer Res* 66:3859-3868.

40. Spira, A., and Ettinger, D. S. 2004. Multidisciplinary management of lung cancer. *N Engl J Med* 350:379-392.

41. Sakai, A., Koga, T., Lim, J. H., Jono, H., Harada, K., Szymanski, E., Xu, H., Kai, H., and Li, J. D. 2007. The bacterium, nontypeable *Haemophilus influenzae*, enhances host antiviral response by inducing Toll-like receptor 7 expression: evidence for negative regulation of host anti-viral response by CYLD. *FEBS J* 274:3655-3668.

42. Swann, J. B., and Smyth, M. J. 2007. Immune surveillance of tumors. *J Clin Invest* 117:1137-1146.

43. Leifer, C. A., Kennedy, M. N., Mazzoni, A., Lee, C., Kruhlak, M. J., and Segal, D. M. 2004. TLR9 is localized in the endoplasmic reticulum prior to stimulation. *J Immunol* 173:1179-1183.
44. Préhaud, C., Mégret, F., Lafage, M., and Lafon, M. 2005. Virus infection switches TLR-3-positive human neurons to become strong producers of beta interferon. *Journal of Virology* 79:12893-12904.
45. Samanta, A. K., Huang, H. J., Bast, R. C., and Liao, W. S. 2004. Overexpression of MEKK3 confers resistance to apoptosis through activation of NFkappaB. *J Biol Chem* 279:7576-7583.
46. Watanabe, K., Hasegawa, Y., Yamashita, H., Shimizu, K., Ding, Y., Abe, M., Ohta, H., Imagawa, K., Hojo, K., Maki, H., et al. 2004. Vasohibin as an endothelium-derived negative feedback regulator of angiogenesis. *J Clin Invest* 114:898-907.
47. Nakamura, E. S., Koizumi, K., Kobayashi, M., Saitoh, Y., Arita, Y., Nakayama, T., Sakurai, H., Yoshie, O., and Saiki, I. 2006. RANKL-induced CCL22/macrophage-derived chemokine produced from osteoclasts potentially promotes the bone metastasis of lung cancer expressing its receptor CCR4. *Clin Exp Metastasis* 23:9-18.
48. Görögh, T., Maune, S., Lippert, B. M., Rudert, H., Gottschlich, S., Hoffmann, M., Meyer, J., Heidorn, K., and Werner, J. A. 2001. Transcriptional repression of the human fibronectin gene in laryngeal squamous cell carcinoma cells. *J Cancer Res Clin Oncol* 127:166-172.
49. Hasan, U. A., Caux, C., Perrot, I., Doffin, A. C., Menetrier-Caux, C., Trinchieri, G., Tommasino, M., and Vlach, J. 2007. Cell proliferation and survival induced by Toll-like receptors is antagonized by type I IFNs. *Proc Natl Acad Sci USA* 104:8047-8052.
50. Hasan, U. A., Trinchieri, G., and Vlach, J. 2005. Toll-like receptor signaling stimulates cell cycle entry and progression in fibroblasts. *J Biol Chem* 280:20620-20627.
51. Kanzler, H., Barrat, F. J., Hessel, E. M., and Coffman, R. L. 2007. Therapeutic targeting of innate immunity with Toll-like receptor agonists and antagonists. *Nat Med* 13:552-559.
52. Schön, M., and Schön, M. 2008. TLR7 and TLR8 as targets in cancer therapy. *Oncogene* 27:190-199.
53. Stary, G., Bangert, C., Tauber, M., Strohal, R., Kopp, T., and Stingl, G. 2007. Tumoricidal activity of TLR7/8-activated inflammatory dendritic cells. *J Exp Med* 204:1441-1451.
54. Dummer, R., Hauschild, A., Becker, J., Grob, J., Schadendorf, D., Tebbs, V., Skalsky, J., Kaehler, K., Moosbauer, S., Clark, R., et al. 2008. An Exploratory Study of Systemic Administration of the Toll-like Receptor-7 Agonist 852A in Patients with Refractory Metastatic Melanoma. *Clinical Cancer Research* 14:856-864.
55. Dieu-Nosjean, M. C., Antoine, M., Danel, C., Heudes, D., Wislez, M., Poulot, V., Rabbe, N., Laurans, L., Tartour, E., de Chaisemartin, L., Lebecque, S., Fridman, W. H., and Cadranel, J. 2008. Long-term survival for NSCLC patients with intra-tumoral lymphoid structures. *J. Clin. Oncology*; in press.
56. Tomai, M. A., Miller, R. L., Lipson, K. E., Vasilakos, J. P., Wolfe, S. L. 2006. Immune response modifiers: Imiquimod and future drugs for modulating the immune response. *Drug Discovery Today* 3:343-352.
57. Robbins, M., Judge, A., Liang, L., McClintock, K., Yaworski, E., MacLachlan, I. 2007. 2'-O-methyl-modified RNAs act as TRL7 antagonists. *Molecular Therapy.* 1-7.

The invention claimed is:

1. A method for treating a cancer patient who does not express TLR7 in cancer cells comprising
    determining whether said cancer patient expresses TLR7 in cancer cells; and
    administering a therapeutically effective amount of an agonist of TLR7 if said cancer patient does not express TLR7 in cancer cells.
2. The method of claim 1 wherein said agonist is used in combination with an anti-cancer agent.
3. The method of claim 1, wherein said cancer is selected from the group consisting of lung cancer, breast cancer, colorectal cancer, renal carcinoma, prostate cancer, melanoma, and lymphoma.
4. The method of claim 1, wherein said cancer is a solid cancer.

* * * * *